United States Patent [19]

Sugimoto et al.

[11] Patent Number: 4,765,990
[45] Date of Patent: Aug. 23, 1988

[54] SUSTAINED-RELEASE NIFEDIPINE PREPARATION

[75] Inventors: Isao Sugimoto, Nara; Kazunori Togo, Ibaraki; Kozo Sasaki, Osaka; Atsushi Yamagata, Osaka; Akira Kuchiki, Osaka, all of Japan

[73] Assignee: Kanebo, Ltd, Tokyo, Japan

[21] Appl. No.: 41,663

[22] Filed: Apr. 21, 1987

Related U.S. Application Data

[63] Continuation of Ser. No. 666,329, filed as PCT JP83/00070 on Mar. 5, 1983, published as WO84/03440 on Sep. 13, 1984, abandoned.

[51] Int. Cl.$^4$ .......................... A61K 9/14; A61K 9/26; A61K 9/52; A61K 9/58
[52] U.S. Cl. ........................................ 424/494; 424/78
[58] Field of Search .................................. 424/494, 78

[56] References Cited

U.S. PATENT DOCUMENTS

| | | | |
|---|---|---|---|
| 4,340,582 | 7/1982 | Kriesel et al. | 424/35 |
| 4,343,789 | 8/1982 | Kawata et al. | 424/19 |
| 4,404,183 | 9/1983 | Kawata et al. | 424/19 |

Primary Examiner—Michael R. Lusignan
Attorney, Agent, or Firm—Wegner & Bretschneider

[57] ABSTRACT

A novel sustained-release nifedipine preparation which comprises the following Composition (A) and Composition (B) in a ratio of 15:85 to 50:50 by weight of nifedipine, Composition (A): a rapid-release preparation containing as an active ingredient nifedipine fine powder having an average particle size of not more than 5μ, Composition (B): a delayed-release preparation containing as the active ingredient nifedipine fine powder having an average particle size of not more than 5μ and having a surface coating layer comprising a non-toxic, hardly water-soluble substance and an enteric high molecular compound.

5 Claims, 3 Drawing Sheets

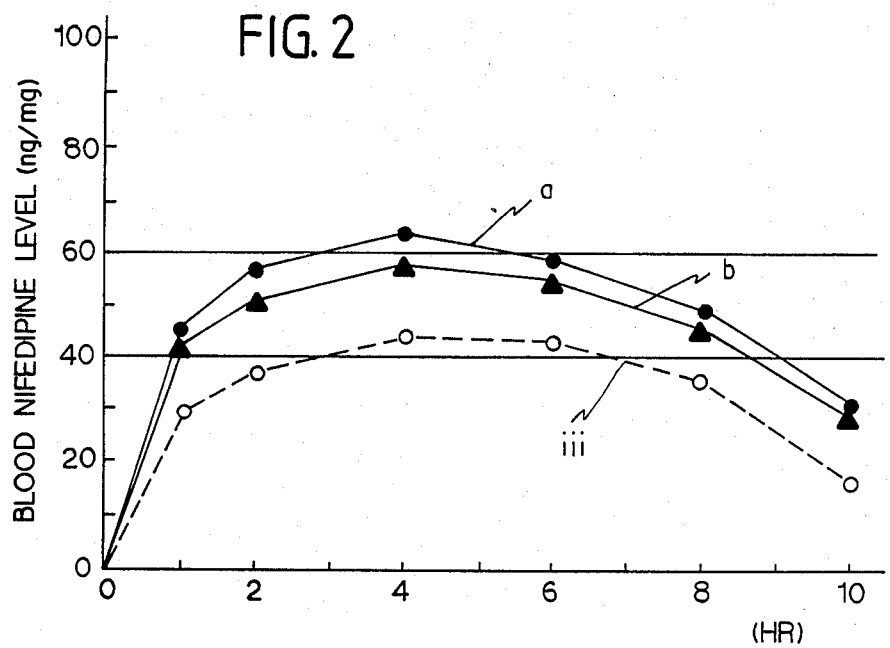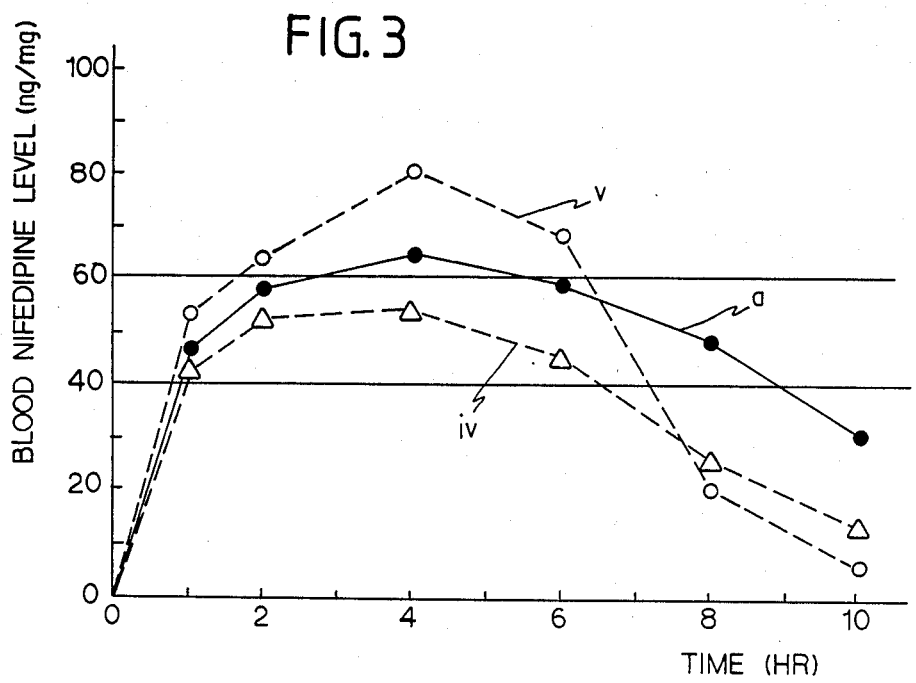

SUSTAINED-RELEASE NIFEDIPINE PREPARATION

This application is a continuation of U.S. application Ser. No. 666,329, filed as PCT JP83/00070 on Mar. 5, 1983, published as WO84/03440 on Sep. 13, 1984, now abandoned.

The present invention relates to a novel preparation of nifedipine, more particularly, to an easily absorbable, sustained-release preparation of nifedipine.

Nifedipine has excellent coronary vasodilating and hypotensive activities, but on the other hand, it has such drawbacks that it is hardly soluble in water and has less absorbability in body liquids, and further that it is rapidly metabolized and excreted.

Nifedipine has now been widely used as a medicine for the treatment of angina pectoris, and since the attack of angina pectoris suddenly occurs, it is required to be administered immediately when the patient is attacked by the disease and further the drug should exhibit its activity rapidly after administered. From this viewpoint, it has been proposed to prepare easily absorbable (rapid-action) preparations of nifedipine. For instance, a preparation is prepared by dissolving nifedipine in liquid polyethylene glycol and packing the solution in soft capsule (cf. Japanese Patent First Publication No. 28621/1973), and nifedipine is formed in a solid solution preparation (cf. Kiso-to-Rinsho, Vol. 18, page 1648, 1979).

These easily absorbable preparations are in fact useful for the treatment of angina pectoris, because nifedipine is easily absorbed within the body and the blood level of nifedipine becomes rapidly high level. However, in such easily absorbable preparations, nifedipine is undesirably rapidly metabolized and excreted, and hence, the blood level is rapidly lowered.

Nifedipine is useful not only for the treatment of angina pectoris, but also for the prophylaxis of angina pectoris and further for the treatment of hypertension. For the latter purpose, it is required that an effective blood level of nifedipine is maintained for a long period of time in addition to the easy absorption thereof.

An object of the present invention is to provide a nifedipine preparation which shows good absorbability of nifedipine and can maintain the therapeutically effective blood level of nifedipine for a long period of time by one time administration, i.e. a nifedipine preparation having both easy absorbability and sustained-release.

Another object of the present invention is to provide a nifedipine preparation suitable for the prophylaxis and treatment of angina pectoris and hypertension.

That is, the present invention relates to a sustained-release nifedipine preparation which comprises the following Compositions (A) and (B) in a ratio of 15:85–50:50 by weight of nifedipine.

Composition (A): a rapid-release preparation containing as an active ingredient nifedipine fine powder having an average particle size of not more than 5μ.

Composition (B): a delayed-release preparation containing as the active ingredient nifedipine fine powder having an average particle size of not more than 5μ and having a surface coating layer comprising a non-toxic, hardly water-soluble substance and an enteric high molecular compound.

The rapid-release preparation means the above nifedipine fine powder per se or a conventional preparation prepared by subjecting a mixture of said fine powder with a conventional pharmaceutically acceptable carrier to granulation or fine granulation procedure. The delayed-release preparation is a preparation prepared by applying a specific release-sustaining means to the same preparation as the above rapid-release preparation. The effectiveness and characteristics of the present composition comprising such Composition (A) and Composition (B) are made clear from the comparison of blood level of nifedipine in case of administration of Preparation a of the present invention (Example 1), a conventional solid solution preparation (Reference Preparation i) and a conventional fine powder granulation preparation of nifedipine (Reference Preparation ii) (cf. Experiment 1, FIG. 1).

BRIEF DESCRIPTION OF THE DRAWINGS

FIG. 2 illustrates the level of nifedipine in blood as a function of time for (a) a nifedipine fine powder that is representative of the present invention, having an average particle size of 2.1μ; (b) a nifedipine fine powder that is representative of the present invention, having an average particle size of 5.0μ; and (iii) a nifedipine fine powder having an average particle size of 9.6μ.

FIG. 3 illustrates the level of nifedipine in blood as a function of time for (a) a preparation that is representative of the present invention of a combination of a rapid-release nifedipine preparation and a separate delayed-release formulation; (iv) a delayed-release nifedipine preparation; and (v) a rapid-release nifedipine preparation.

That is, FIG. 1 shows change of blood level of nifedipine after orally administering the above three kinds of preparations containing each 20 mg of nifedipine to Beagle dogs. As is clear from the results, the solid solution preparation (Reference Preparation i) and fine powder granulation preparation (Reference Preparation ii) showed rapid increase of the blood level when administered, and the blood level became very high level, but it rapidly lowered. Such an initial high level is unfavorable in view of side effect, and further, such a rapid lowering of blood level is not suitable in view of release sustaining.

Figure 1:
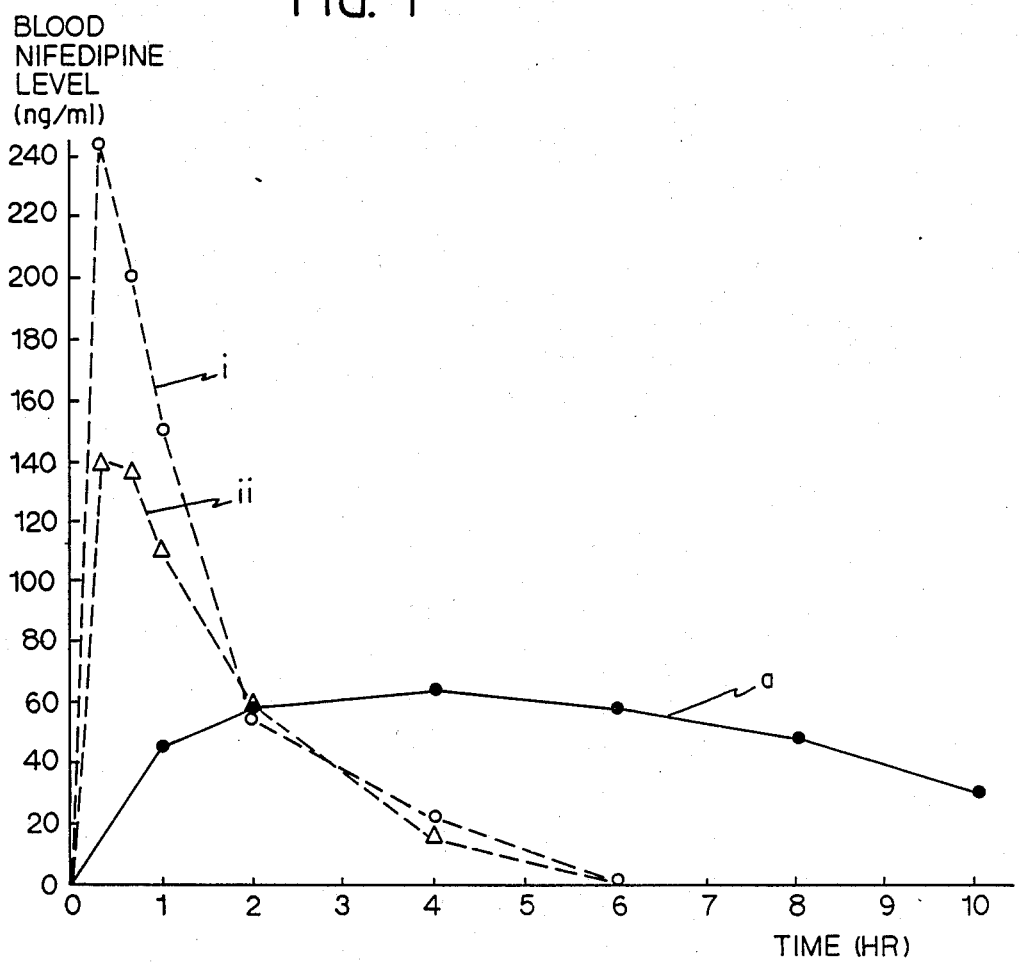
FIG. 1 illustrates the level of nifedipine in blood as a function of time for (a) a preparation that is representative of the present invention; (i) a conventional solid solution preparation; and (ii) a conventional fine powder granulation preparation.

On the contrary, Preparation a of the present invention showed a very plane pattern in the blood level curve, i.e. the blood level of nifedipine was maintained in the range of 40 to 60 ng/ml from 1 to 9 hours after the administration (totally for 8 hours), and further, at the first stage after administration, the blood level satisfactorily increased. Thus, it is clear that this preparation is suitable as a sustained-release preparation.

The preparation of the present invention and method for preparing the same are explained in more detail below.

Firstly, in the preparation of the present invention, it is characteristic to employ as the active ingredient nifedipine fine powder having an average particle size of not more than $5\mu$, preferably 1 to $4\mu$.

Such a nifedipine fine powder can be obtained by pulverizing the conventional crystalline nifedipine (average particle size thereof is usually more than $30\mu$) by conventional methods using ball-mill, jet-mill, or automated mortar, optionally followed by subjecting to screening.

In addition to the application of specific release-sustaining means disclosed hereinafter, the above feature of average particle size of not more than $5\mu$ is important for satisfying two requirements of the easy absorption of the medicament and the maintaining of the high blood level of the medicament.

That is, as is clear from FIG. 2 which shows change of blood level of nifedipine after administering to Beagle dogs the preparations prepared from nifedipine fine powders having an average particle size of $2.1\mu$, $5.0\mu$ and $9.6\mu$ [Preparation a of the present invention, Preparation b of the present invention, and Reference Preparation iii (cf. Experiment 2), respectively], Preparation a (nifedipine average particle size: $2.1\mu$) and Preparation b (said size: $5.0\mu$) of the present invention showed a blood nifedipine level of more than 40 ng/ml one hour after the administration and could maintain the blood level at the range of about 40 to 60 ng/ml for 8 to 9 hours after the administration, but on the contrary, Reference Preparation iii (said size: $9.6\mu$) required about 3 hours after administration for increasing the blood nifedipine level to 40 ng/ml, and the level lowered to less than 40 ng/ml after about 7 hours. Thus, it is inferior in both the absorbability and the release sustaining properties.

In the preparation of a sustained-release preparation of nifedipine, an easily absorbable nifedipine solid solution may be used as the active ingredient after making a part thereof in the sustained-release form, but according to the present inventors' study, when the solid solution is made in the sustained-release form, it is wetted within the peptic truct when administered, which results in crystallization of nifedipine and then tends to lowering of absorption, and hence, it can hardly maintain the desired blood nifedipine level for a long period of time. Thus, it has first been found that the practically useful sustained-release nifedipine preparation can be prepared by using nifedipine fine powder having an average particle size of not more than $5\mu$.

Another characteristic of the present preparation is that the rapid-release preparation (Composition A) is prepared by using the above nifedipine fine powder and separately the delayed-release preparation (Composition B) is prepared by subjecting the rapid-release preparation to the specific release sustaining means as mentioned hereinafter, and then both compositions are incorporated in a fixed ratio.

As defined above, Composition (A) is the nifedipine fine powder per se, or a preparation obtained by admixing the fine powder with pharmaceutically acceptable carriers such as excipients, filling agents, binding agents, etc., followed by subjecting the mixture to the conventional granulation or fine granulation procedure. This Composition (A) can rapidly release the easily absorbable nifedipine fine powder when administered and can give early increase of the blood nifedipine level.

On the other hand, Composition (B) is obtained by firstly preparing a granule or fine granule of the nifedipine fine powder like in the above Composition (A) and then coating the granule with a coating layer comprising a pharmaceutically acceptable, hardly water-soluble substance (hereinafter, referred to merely as "hardly soluble substance) and an enteric high molecular compound. It is one of the important characteristics of the present invention to use as the coating layer a mixture of the hardly soluble substance and the enteric high molecular compound, by which the desired slow- and sustained-release of nifedipine is effected and then the fixed blood nifedipine level can be maintained for a long period of time. Instead of the above, when the hardly soluble substance or the enteric high molecular compound is used alone for the coating, and when such a coated preparation thus obtained is combined with Composition (A), the former case (Reference Preparation iv) shows too slow release of nifedipine and hence the utilizing ratio of nifedipine is decreased, and on the other hand, in the latter case (Reference Preparation v) shows too rapid release of nifedipine and hence the blood nifedipine level is rapidly lowered. Thus, both preparations can not exhibit the desired effects as in the preparation of the present invention (Preparation a) (cf. Experiment 3, FIG. 3). Representative examples of the hardly soluble substance used in Composition (B) are fats and oils and ethyl cellulose. The fats and oils are, for example, hardened oils as defined in Japan Pharmacopeia, 10th Edition, or glycerin fatty acid esters as defined in Foodstuff Additives Regulation, 4th Edition, or the like. The hydrogenated oils include, for example, hydrogenated products of fish oil, whale oil or soybean oil. The glycerin fatty acid esters include anyone of mono-, di- or tri-ester. These hardly soluble substances may be used in combination of two or more thereof.

The enteric high molecular compound includes cellulose acetate phthalate, hydroxypropylmethyl cellulose phthalate, methacrylic acid-methyl methacrylate copolymer, etc. which are usually used for enteric preparations. They may also be used in combination of two or more thereof.

The above hardly soluble substances and enteric high molecular compounds can be combined in various ways. Preferred combinations are, for example, a combination of a hydrogenated oil and hydroxypropylmethyl cellulose phthalate, a combination of a hydrogenated oil and methacylic acid-methyl methacrylate copolymer, a combination of glycerin monostearate and hydroxypropylmethyl cellulose phthalate, or the like. The mixing ratio may somewhat vary depending on the kinds of the hardly soluble substances and the enteric high molecular compounds, but they are usually mixed in the weight ratio of 1:5 to 5:1, particularly 1:2 to 2:1 of the hardly soluble substance:the enteric high molecular compound.

The coating is carried out by dissolving the above hardly soluble substance and enteric high molecular compound in a common solvent (e.g. ethanol, dichloromethane, etc.) and then coating the solution onto the granules or fine granules obtained above by a conventional coating method, such as pan coating, fluidized bed coating, or the like.

The coating amount varies depending on the components of the coating layer, shape and particle size of the substance to be coated and is not specified, but is usually in the range of 7 to 100% by weight (calculated in the increase ratio of the solid components).

The preparation of the present invention is prepared from the above-prepared Composition (A) and Composition (B). In the preparation, Composition (A) and Composition (B) are incorporated in the ratio of 15:85 to 50:50, preferably 20:80 to 40:60, by weight of nifedipine. When the mixing ratio of both compositions is outside the above-mentioned ratio, the initial blood level is not sufficiently raised and/or the blood level is not sufficiently maintained, and hence, the desired sustained-release preparation can not be obtained (cf. Experiment 4, FIG. 4).

The preparation of the present invention is preferably in the non-compressed form, and particularly preferably, both Composition (A) and Composition (B) are prepared in the form of a granule or fine granule and are simply mixed, or the granular or fine granular compositions are packed in capsules to obtain a capsule preparation. Besides, both Compositions (A) and (B) may be simultaneously administered without previously making in one-pack preparation. Such an embodiment is also included within the present invention.

The usage and dosage of the preparation of the present invention may vary according to the object for use or the subject to be administered, but in case of Preparation a of the present invention as disclosed in Example 1 hereinafter, for example, it can maintain the minimum effective blood level of nifedipine, 30 ng/ml for about 9 hours only by one time administration of one capsule (cf. Experiment 5, FIG. 5). Accordingly, this may be used as an index for determining the effective usage and dosage.

That is, in case of Preparation a of the present invention (a capsule containing 20 mg of nifedipine), it is usually administered in a dose of one capsule per each time at an interval of 8 to 12 hours for the prophylaxis and treatment of angina pectoris and hypertension.

The present invention is illustrated by the following Examples and Experiments in more detail.

EXAMPLE 1

Capsules (1) Preparation of Composition (A)

[A-1]: To a mixture of nifedipine fine powder having an average particle size of 2.1μ (200 g), lactose (150 g), corn starch (80 g), crystalline cellulose (250 g) and carboxymethyl cellulose calcium (300 g) is added an aqueous solution of hydroxypropyl cellulose (20 g), and the mixture is well kneaded. The mixture is granulated with a cylindrical granulating machine and then is formed in a round shape with a Marumerizer, and dried at 50° C. for 12 hours to give granules containing nifedipine of 20 mg/100 mg (particle size: 12-32 mesh).

[A-2]: In the same manner as described in the above [A-1] except that nifedipine fine powder having an average particle size of 5.0μ is used, there are prepared granules containing nifedipine of 20 mg/100 mg (particle size: 12-32 mesh).

(2) Preparation of Composition (B)

[B-1]: Composition [A-1] (500 g) obtained above is entered in a coating pan and is subjected to spray coating using a coating liquid consisting of hydroxypropyl methyl cellulose phthalate (tradename, HP-55, manufactured by Shinetsu Kagaku K.K.) (400 g), glycerin monostearate (400 g), triacetine (70 g), ethanol (4,500 g) and dichloromethane (4,630 g) until the weight of granules becomes 880 g to give coated granules.

[B-2]: In the same manner as described in the above [B-1] except that Composition [A-2] (500 g) is used instead of Composition [A-1] (500 g), there are prepared coated granules.

[B-3]: In the same manner as described in the above [B-1] except that the coating liquid contains a hydrogenated oil (Japan Pharmacopeia 10 Edition) (300 g) instead of glycerin monostearate (400 g), there are prepared coated granules.

(3) Preparation of capsules (a preparation of the present invention)

Composition (A) and Composition (B) obtained above are mixed in the ratios as shown in Table 1, and each mixture is packed into 3# hard capsules to give 5 kinds of capsules wherein nifedipine is contained in an amount of 20 mg per each capsule (Preparation a, b, c, d and e of the present invention).

TABLE 1

| Preparation | Compositions | | Mixing ratio* | |
|---|---|---|---|---|
| | Composition (A) | Composition (B) | Composition (A) | Composition (B) |
| a | A-1 | B-1 | 30 | 70 |
| b | A-2 | B-2 | 30 | 70 |
| c | A-1 | B-3 | 15 | 85 |
| d | " | " | 30 | 70 |
| e | " | " | 50 | 50 |

*Based on the weight of nifedipine

EXAMPLE 2

Granules (1) Preparation of Composition (A)

To a mixture of nifedipine fine powder having an average particle size of 2.2μ (10 g), lactose (200 g) and corn starch (180 g) is added an aqueous solution of hydroxypropyl cellulose (10 g), and the mixture is kneaded and granulated, dried at 60° C. for one hour and then subjected to screening to give granules (particle size: 14-24 mesh).

(2) Preparation of Composition (B)

In the same manner as described in the above (1), there are prepared granules (particle size: 14-24 mesh) by using nifedipine fine powder having an average particle size of 2.2μ (20 g), lactose (500 g), corn starch (450 g) and hydroxypropyl cellulose (30 g). The granules (500 g) thus prepared are entered into a coating pan and is subjected to spray coating using a coating liquid consisting of methacrylic acid-methyl methacrylate copolymer (tradename, Eudragit ® L, manufactured by Rohm Pharm.) (50 g), glycerin monostearate (40 g), and ethanol (1,000 g) until the weight of granules becomes 800 g to give coated granules.

(3) Preparation of granules (a preparation of the present invention)

Composition (A) (200 g) and Composition (B) (800 g) prepared above are well mixed, and the mixture (each 1 g) is folded in a powder paper to give folded granules wherein each granule contains 5 mg of the rapid-release nifedipine and 10 mg of delayed-release nifedipine (totally 15 mg).

EXAMPLE 3

Granules

In the same manner as described in Example 2 except that the coating liquid in Example 2-(2) [Preparation of Composition (B)] contains ethyl cellulose (50 g) instead of glycerin monostearate (40 g), there are prepared folded granules wherein each granule contains 5 mg of the rapid-release nifedipine and 10 mg of delayed-release nifedipine.

EXPERIMENTS 1-4

Blood nifedipine level when administered to Beagle dogs

As to the preparations prepared in the above Examples 1 to 3, the change of blood nifedipine level with lapse of time was studied by administering them to Beagle dogs.

Test method: The test preparation (20 mg as nifedipine) was orally administered to Beagle dogs (weighing 8-11 kg, one group: 5 dogs). After bleeding at an interval, the blood nifedipine level was measured by ECD gas chromatography. The results are shown in the average of the data obtained in five dogs.

(Experiment 1) Comparison between the preparation of the present invention and the easily absorbable solid solution preparation and easily absorbable fine powder preparation:

A. Preparation to be tested (1) Preparation a of the present invention prepared in Example 1

(2) Easily absorbable solid solution preparation (Reference Preparation i)

It is a granule preparation (containing nifedipine of 20 mg per 1 g) which is prepared by entering fine granulated sugar (920 g) into a spray granulating machine and then spray coating it with a solution of nifedipine (20 g) and polyvinylpyrrolidone (average molecular weight: 40,000) (60 g) in dichloromethane.

(3) Easily absorbable fine powder preparation (Reference Preparation ii)

It is Composition [A-1] prepared in Example 1

B. Results of the experiment

The change of the blood nifedipine level with lapse of time after each preparation was administered is shown in the accompanying FIG. 1.

Besides, when the granule preparations as prepared in Example 2 and Example 3 were administered to Beagle dogs, they showed almost similar change of the blood nifedipine level to that of Preparation a of the present invention as shown in FIG. 1, and in both cases, the blood level of 40 to 60 ng/ml was maintained for about 8 hours from one hour after the administration.

(Experiment 2) Average particle size of nifedipine and change of blood nifedipine level:

A. Compositions to be tested (1) Preparation a of the present invention prepared in Example 1 (using nifedipine having an average particle size of $2.1\mu$)

(2) Preparation b of the present invention prepared in Example 1 (using nifedipine having an average particle size of $5.0\mu$)

(3) Reference Preparation iii (using nifedipine having an average particle size of $9.6\mu$) as mentioned below In the same manner as in the preparation of Preparation a of the present invention as described in Example 1 except that nifedipine fine powder having an average particle size of $9.6\mu$, there were prepared capsules (each one capsule containing 20 mg of nifedipine).

B. Results of the experiment

The change of the blood nifedipine level when the above three preparations were administered is shown in the accompanying FIG. 2.

(Experiment 3) Components of the coating layer and the change of the blood nifedipine level A. Compositions to be tested (1) Preparation a of the present invention prepared in Example 1 (using together a hardly soluble substance and an enteric high molecular compound)

(2) Reference Preparation iv (using a hardly soluble substance alone) as mentioned below The same Composition [A-1] as in Example 1 and a delayed-release Composition [B'-1] prepared as described below were mixed in a ratio of 30:70 (w/w) (as the weight of nifedipine), and the mixture was packed in 3# hard capsule to give capsules (each one capsule containing 20 mg of nifedipine).

Preparation of a delayed-release Composition [B'-1]:

It was prepared in the same manner as in the preparation of the Composition [B-1] as described in Example 1 except that the coating liquid contains glycerin monostearate (500 g) alone instead of hydroxypropyl methyl cellulose phthalate (400 g) and glycerin monostearate (400 g).

(3) Reference Preparation v (using an enteric high molecular compound alone) as mentioned below The same Composition [A-1] as in Example 1 and a delayed-release Composition [B'-2] prepared as described below were mixed in a ratio of 30:70 (w/w) (as the weight of nifedipine), and the mixture was packed in 3# hard capsule to give capsules (each one capsule containing 20 mg of nifedipine).

Preparation of a delayed-release Composition [B'-2]:

It was prepared in the same manner as in the preparation of the Composition [B-1] as described in Example 1 except that the coating liquid contains hydroxypropyl methyl cellulose phthalate (500 g) alone instead of hydroxypropyl methyl cellulose phthalate (400 g) and glycerin monostearate (400 g).

B. Results of the experiment

The change of the blood nifedipine level with lapse of time after each preparation was administered is shown in the accompanying FIG. 3.

(Experiment 4) Mixed ratio of Composition (A) and Composition (B) and the change of the blood nifedipine level A. Compositions to be tested (1) Reference Preparation vi [rapid-release nifedipine:delayed release nifedipine=10:90 (w/w)] as prepared below Composition [A-1] and Composition [B-3] as prepared in Example 1 were mixed in a ratio of 10:90 (w/w) (calculated as the weight of nifedipine), and the mixture was packed in 3# hard capsule to give capsules (each one capsule containing 20 mg of nifedipine).

(2) Preparation c of the present invention as prepared in Example 1 [rapid release nifedipine:delayed-release nifedipine=15:85 (w/w)]

(3) Preparation d of the present invention as prepared in Example 1 [rapid-release nifedipine:delayed-release nifedipine=30:70 (w/w)]

(4) Preparation e of the present invention as prepared in Example 1 [rapid-release nifedipine:delayed-release nifedipine=50:50 (w/w)]

(5) Reference Preparation vii [rapid-release nifedipine:delayed-release nifedipine=60:40 (w/w)] as prepared below Composition [A-1] and Composition [B-3] as prepared in Example 1 were mixed in a ratio of 60:40 (w/w) (calculated as the weight of nifedipine), and the mixture was packed in 3# hard capsule to give capsules (each one capsule containing 20 mg of nifedipine).

B. Results of the experiment

Figure 4:
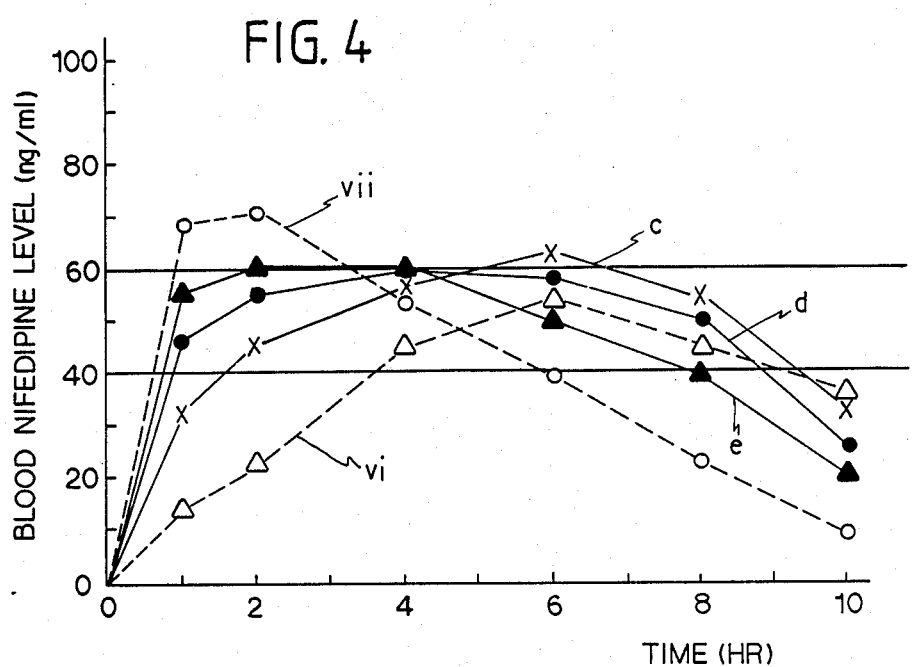
FIG. 4 illustrates the level of nifedipine in blood as a function of time for (c) a preparation that is representative of the present invention containing rapid-release nifedipine:delayed-release nifedipine=15:85; (d) a preparation that is representative of the present invention containing rapid-release nifedipine:delayed-release nifedipine=30:70; (e) a preparation that is representative of the present invention containing rapid-release nifedipine:delayed-release nifedipine=50:50; (vi) a preparation containing rapid-release nifedipine:delayed-release nifedipine=10:90; and (vii) a preparation containing rapid-release nifedipine:delayed-release nifedipine=60:40.

The change of the blood nifedipine level with lapse of time after each preparation was administered is shown in the accompanying FIG. 4.

EXPERIMENT 5

Blood nifedipine level when administered to human

In order to make clear effectiveness of the preparation of the present invention when administered to human, Preparation a of the present invention and Reference Preparation i were administered to human and change of the blood nifedipine level was measured.

A. Test method

Preparation a of the present invention (20 mg, calculated as nifedipine) and Reference Preparation i (10 mg, calculated as nifedipine) were each administered to healthy male adult (4 men), and after the administration, blood was collected an an interval with the lapse of time, and the blood nifedipine level was measured by ECD gas chromatography. The results are shown in average of four test persons.

B. Results of the test

Figure 5:
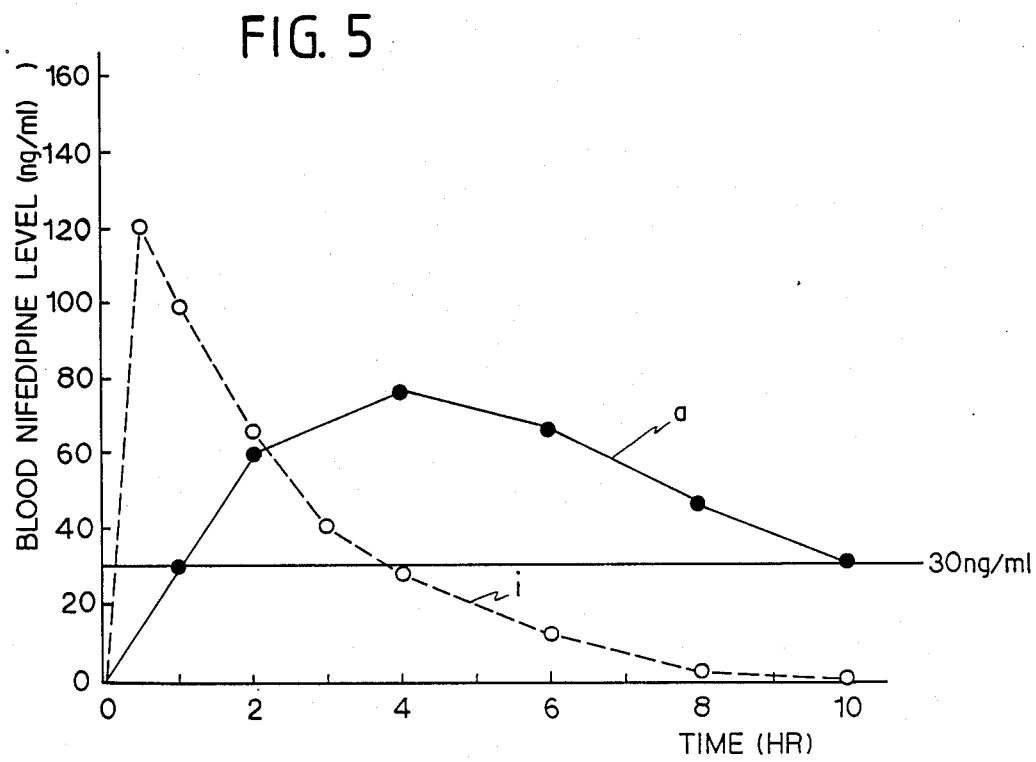
FIG. 5 illustrates the level of nifedipine in the blood of a human as a function of time for (a) a preparation that is representative of the present invention; and (i) a conventional solid solution preparation.

The results are shown in FIG. 5. According to the results shown in FIG. 5, when Preparation a of the present invention was administered, the blood nifedipine level was 30 ng/ml which is minimum effective blood level in human or higher than it, and the blood level was maintained from one hour to 10 hour after the administration, i.e. for about 9 hours. It is clear from this that the preparation of the present invention is useful as a sustained-release nifedipine preparation.

We claim:

1. A non-compressed sustained-release nifedipine preparation consisting essentially of the following Composition (A) and Composition (B) in a ratio of 15:85 to 50:50 by weight of nifedipine, Composition (A): a rapid-release preparation containing as an active ingredient nifedipine crystalline fine powder having an average particle size of not more than 5 microns in admixture with a pharmaceutically acceptable carrier, Composition (B): a delayed-release preparation containing as the active ingredient nifedipine fine powder having an average particle size of not more than 5 microns and having a surface coating layer comprising a non-toxic, hardly water-soluble substance selected from the group consisting of ethyl cellulose, hydrogenated soybean oil and glycerin monostearate, and an enteric high molecular compound selected from the group consisting of cellulose acetate phthalate, hydroxypropylmethyl cellulose phthalate and methacrylic acid methyl methacrylate copolymer in a weight ratio of 1:5 to 5:1.

2. The sustained-release nifedipine preparation according to claim 1, wherein the nifedipine fine powder has an average particle size of 1 to 4 microns.

3. The sustained-release nifedipine preparation according to claim 2, wherein the nifedipine fine powder has an average particle size of about 2 microns.

4. The sustained-release nifedipine preparation according to claim 1, wherein the hardly water-soluble substance and the enteric high molecular compound are mixed in a ratio of 1:2 to 2:1 by weight.

5. The sustained-release nifedipine preparation according to claim 1, wherein Composition (A) and Composition (B) are mixed in a ratio of 20:80 to 40:60 by weight of nifedipine.

* * * * *